United States Patent
Gordon et al.

(10) Patent No.: US 7,783,433 B2
(45) Date of Patent: Aug. 24, 2010

(54) AUTOMATED DEFECT DETECTION OF CORROSION OR CRACKS USING SAFT PROCESSED LAMB WAVE IMAGES

(75) Inventors: Grant A. Gordon, Peoria, AZ (US); Radek Hedl, Jedovnice (CZ)

(73) Assignee: Honeywell International Inc., Morristown, NJ (US)

( * ) Notice: Subject to any disclaimer, the term of this patent is extended or adjusted under 35 U.S.C. 154(b) by 293 days.

(21) Appl. No.: 11/880,450

(22) Filed: Jul. 21, 2007

(65) Prior Publication Data

US 2008/0289423 A1 Nov. 27, 2008

Related U.S. Application Data

(60) Provisional application No. 60/939,495, filed on May 22, 2007.

(51) Int. Cl.
G01B 5/28 (2006.01)

(52) U.S. Cl. ............................... 702/39; 700/175

(58) Field of Classification Search ............... 702/34, 702/35, 39, 56; 700/175, 176; 382/108, 382/152, 173
See application file for complete search history.

(56) References Cited

U.S. PATENT DOCUMENTS

| | | | |
|---|---|---|---|
| 4,646,572 A | 3/1987 | Bottger et al. |
| 4,653,000 A | 3/1987 | Matsumoto |
| 4,911,014 A | 3/1990 | Lund et al. |
| 5,029,475 A | 7/1991 | Kikuchi et al. |
| 5,425,867 A | 6/1995 | Dawson et al. |
| 5,493,511 A | 2/1996 | Wincheski et al. |
| 5,528,557 A | 6/1996 | Horn |
| 5,608,814 A | 3/1997 | Gilmore et al. |
| 5,760,904 A | 6/1998 | Lorraine et al. |
| 6,092,420 A | 7/2000 | Kimura et al. |

(Continued)

FOREIGN PATENT DOCUMENTS

EP 0302073 2/1989

(Continued)

OTHER PUBLICATIONS

Martinez, O.; Parrilla, M.; Izquierdo, M.A.G.; Ullate, L.G.; Application of Digital Signal Processing Techniques to Synthetic Aperture Focusing Technique Images; Sensors and Actuators 76 (1999) 448-456, Dec. 4, 1998; Elsevier Science S.A.

(Continued)

*Primary Examiner*—Manuel L Barbee
(74) *Attorney, Agent, or Firm*—Ingrassia Fisher & Lorenz, P.C.

(57) ABSTRACT

A system, method and computer program product is provided for automated defect detection of corrosion or cracks using synthetic aperture focusing technique (SAFT) processed Lamb wave images. The method comprises processing the first image using a synthetic aperture focusing technique (SAFT) to enhance a resolution and a signal to noise ratio of a first extracted ultrasonic image, applying a systemic background noise suppression algorithm to the first extracted ultrasonic image to render a second extracted ultrasonic image having reduced noise, and applying a deconvolution linear filtering process to the second extracted ultrasonic image to render a third extracted ultrasonic image.

26 Claims, 9 Drawing Sheets
(4 of 9 Drawing Sheet(s) Filed in Color)

U.S. PATENT DOCUMENTS

| | | | |
|---|---|---|---|
| 6,182,512 B1 * | 2/2001 | Lorraine | 73/655 |
| 6,264,824 B1 | 7/2001 | Reid et al. | |
| 6,386,038 B1 | 5/2002 | Lewis, III et al. | |
| 6,450,036 B1 | 9/2002 | Ashida et al. | |
| 6,677,765 B2 | 1/2004 | Breen et al. | |
| 6,797,149 B2 | 9/2004 | Eden | |
| 6,843,129 B2 | 1/2005 | Dust | |
| 6,877,376 B1 | 4/2005 | Schuster et al. | |
| 6,996,480 B2 | 2/2006 | Giurgiutiu et al. | |
| 7,054,762 B2 | 5/2006 | Pagano et al. | |
| 7,117,134 B2 | 10/2006 | Dubois et al. | |
| 7,150,193 B2 | 12/2006 | Lorraine et al. | |
| 2002/0029116 A1 | 3/2002 | Sills et al. | |
| 2005/0102109 A1 | 5/2005 | Dubois et al. | |
| 2005/0109110 A1 | 5/2005 | Staszewski | |
| 2005/0228597 A1 | 10/2005 | Giurgiutiu et al. | |
| 2005/0256689 A1 | 11/2005 | Schulz | |
| 2006/0048578 A1 | 3/2006 | Dickinson et al. | |
| 2007/0098245 A1 | 5/2007 | Mylaraswamy et al. | |

FOREIGN PATENT DOCUMENTS

| WO | 02073169 A1 | 9/2002 |
|---|---|---|

OTHER PUBLICATIONS

Levesque, D.; Blouin, A.; Neron, C.; Monchalin, J.P.; Performance of Laser-Ultrasonic F-SAFT Imaging; Ultrasonics 40 (2002) 1057-1063; May 2, 1999; Elsevier Science B.V.

Gordon, G.A.; Braunling, R.; Quantitative Corrosion Monitoring and Detection Using Ultrasonic Lamb Waves; Smart Structures and Materials 2005: Sensors and Smart Structures Technologies for Civil, Mechanical, and Aerospace Systems; SPIE vol. 5765; Bellingham, WA, 2005, XP002491265.

Sicard, R.; Chahbaz, A.; Goyette, J.; Guided Lamb Waves and L-SAFT Processing Technique for Enhanced Detection and Imaging of Corrosion Defects in Plates with Small Depth-to-Wavelength Ratio; IEEE Transactions on Ultrasonics, Ferroelectrics, and Frequency Control, vol. 51, No. 10, Oct. 2004, XP002491266.

EP Search Report, 08156604.4 dated Aug. 20, 2008.

* cited by examiner

AUTOMATED DEFECT DETECTION OF CORROSION OR CRACKS USING SAFT PROCESSED LAMB WAVE IMAGES

CROSS-REFERENCES TO RELATED APPLICATIONS

This application claims the benefit of U.S. Provisional Application No. 60/939,495, filed May 22, 2007.

TECHNICAL FIELD

The present invention generally relates to defect detections in materials and, more particularly, to automated corrosion or crack detection using images generated from applying a synthetic aperture focusing technique to ultrasonic Lamb waves.

BACKGROUND

Corrosion and cracking can present concerns for structures used in aircraft and other aerospace vehicles. In particular, corrosion and cracking can have a significant impact on vehicle maintenance costs and ultimately on continued vehicle operation. Therefore, aerospace vehicle owners and operators spend considerable effort identifying and controlling the growth of structural defects. In some cases, the defects may not be visible by direct inspection, and may only be discovered after a relatively time-consuming structural disassembly has taken place.

Thus, there is a need for a relatively inexpensive sensor and supporting system that can be used to monitor material defects in aircraft and other aerospace vehicle structures, and most notably in hard to reach places. This would allow aircraft owners and operators to detect emerging defects in a much more timely, reliable, and cost-efficient manner. It would also be advantageous if such as system could be well characterized in terms of probability of detection (POD) and probability of false indications (PFI).

BRIEF SUMMARY

The present invention relates to a signal processing system and method that provide robust on-line automatic defect detection, such as corrosion pitting, in a structural health monitoring environment. The system and method detects early stage pitting corrosion of metallic structures using ultrasound images acquired with guided Lamb waves, which are then processed by means of a synthetic aperture focusing technique (SAFT). The system and method estimates probability of detection (POD) and probability of false indication (PFI), and allows flexibility in setting the automated detection levels in relationship to the POD and PFI to support informed damage tolerance maintenance procedures.

In one embodiment, by way of example only, the present invention is an automated method for detecting corrosion or crack defects. A first of a plurality of ultrasound images acquired with guided Lamb waves is obtained. The first image is processed using a synthetic aperture focusing technique (SAFT) to render a first extracted ultrasonic image. A systemic background noise suppression algorithm is applied to the first extracted ultrasonic image to render a second extracted ultrasonic image. A deconvolution linear filtering process is applied to the second extracted ultrasonic image to render a third extracted ultrasonic image. Noise models are developed and adjusted locally to adapt image segmentation and ensuing defect identification to the known image noise distributions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
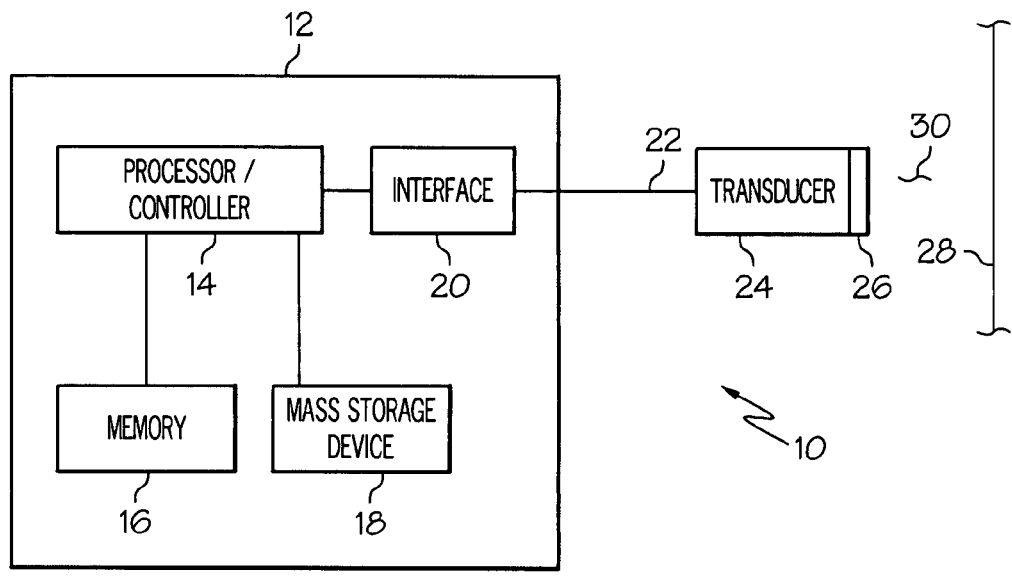
FIG. 1 is an exemplary automated corrosion or crack detection system.

The following detailed description is merely exemplary in nature and is not intended to limit the invention or the application and uses of the invention. Furthermore, there is no intention to be bound by any theory presented in the preceding background or the following detailed description.

Ultrasound is widely used as a powerful technique for nondestructive testing. Furthermore, ultrasonic Lamb waves have been investigated as an approach for inspecting plate-like structures such as the skin of an aircraft. Lamb waves are guided elastic waves that can travel in a solid plate with free boundaries at their top and bottom surfaces. Particle displacement occurs both in the direction of wave propagation and perpendicular to the plane of the plate. During their propagation through the solid plate structure, Lamb waves form several symmetric and antisymmetric modes related to the plate thickness and acoustic frequency of the waves. The phase velocity of these modes is dependent on a number of parameters including frequency and can be described graphically by a set of dispersion curves. The dispersive nature of the Lamb waves can make their interpretation difficult. This fact has limited the applicability of Lamb waves in nondestructive testing applications.

An advantage of the Lamb waves is that they can propagate for long distances in plate structures. Moreover, in contrast to the conventional method where the inspection is made with bulk waves collecting data on a point by point basis, Lamb waves travel along the plate while sensing through the plate thickness. Therefore, Lamb waves can provide significant time savings and can form the basis of an approach to inspect a plate structures without moving the transducer. Even though the ultrasound is an excellent technique for the detection of flaws, it is much less efficient in evaluation of their size, shape and orientation. The spatial resolution and signal to noise ratio of the ultrasound image can be improved by additional numerical processing of the ultrasound data. Such an algorithm can be a Synthetic Aperture Focusing Technique applied to an array of data. The SAFT method takes advantage of the spatial and temporal correlation of data to enhance the resolution and signal to noise ratio of an extracted ultrasonic image.

Although the SAFT was originally developed in the time domain, it can be implemented in the frequency domain using a backpropagation technique based on the angular spectrum approach of scalar diffraction theory. Implementation of the SAFT algorithm in the frequency domain (F-SAFT) allows significant reduction in processing time by limiting the processed data to a selected bandwidth of concern.

SAFT can also be easily modified for use with Lamb waves to account for their dispersive nature. The modification is called an L-SAFT algorithm. Its implementation requires additional computation of the dispersive curve corresponding to actually generated Lamb wave propagation modes. It is convenient to treat one Lamb wave at a time when compensating for dispersion by means of the L-SAFT algorithm. Thus, it is advantageous to generate a dominant Lamb wave mode during the specimen inspection.

A process is disclosed herein that achieves robust automatic detection of defects using synthetic aperture focusing technique (SAFT) ultrasound Lamb wave images. The initial raw, untreated ultrasound SAFT generated images contain several types of degradation in addition to defect evidence. To improve defect detection, noise degradation mechanisms are analyzed, modeled, and treated to reduce their influence on the final image that is used to characterize the defect damage. The noise models for random noise, systematic noise, and point spread function distortion are established prior to on-line operation, and preferably reside in memory. These noise models can be adjusted locally to account for spatial variations within the image field. To further enhance the defect estimate, image fusion may be implemented. Image fusion, if implemented, is followed by image segmentation to identify defect regions. A statistical model for the image random noise is used to adapt the image segmentation and ensuing decision analysis to the known noise distributions. This allows a probability of false indication (noise labeled a flaw) and a probability of detection to be established. Finally, image segments are described with feature vectors so that further decision analysis can be made.

FIG. 1 illustrates an exemplary automated defect detection system 10. A processing device 12 includes a processor/controller 14 coupled to a memory device 16, which can include such memory as non-volatile read only memory (NVRAM) or an equivalent. Processor 14 is also coupled to a mass storage device 18, which can include such devices as hard disk devices (HDDs) or an equivalent. Processor 14 is coupled through an interface 20 using lead 22 to a transducer device 24 with an integrated emitter/sensor 26 in view of a surface 28 to be analyzed, such as a portion of the skin of an airframe. Surface 28 can be comprised of metal, such as aluminum (Al), or can also be comprised of a composite, such as a durable epoxy or carbon fiber material. A series of so-called "Lamb" waves 30 are emitted and received by the transducer 24 as the transducer interrogates the surface 28 for defects. As will be appreciated, system 10 can include a variety of additional components, such as additional transducers 24 which are configured in an array, or additional memory or processing components for a particular application.

Processor/controller 14 may be configured to execute computer instructions which can be stored in memory 16, mass storage 18, or embodied in a computer program product such as a digital versatile disk (DVD) or compact disk (CD) or an equivalent. The computer instructions may include executable commands which incorporate methodologies and algorithms as further described below.

Figure 2:
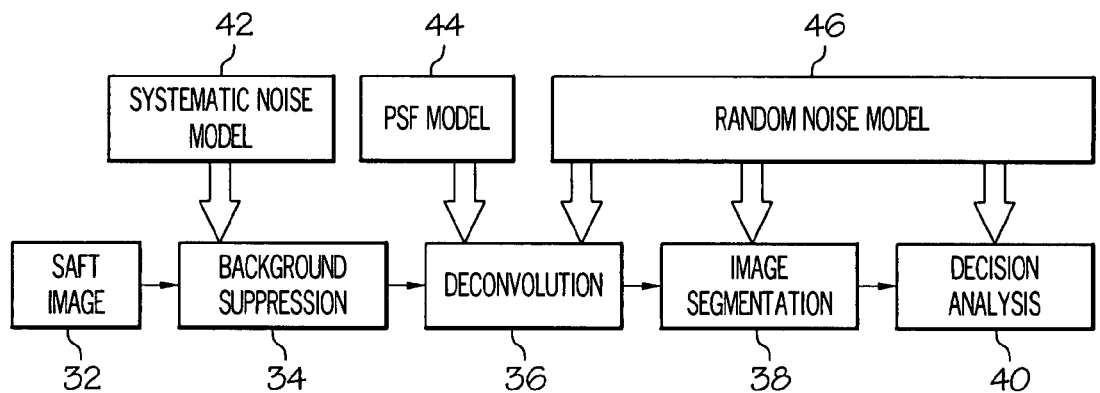
FIG. 2 is a functional block diagram of an automatic corrosion or crack detection algorithm.

The methodology to perform on-line automatic defect detection, such as pitting corrosion detection, according to a particular preferred embodiment that is depicted in FIG. 2, employs four image processing steps and three noise models. The defect detection system 10 first obtains a SAFT image 32. A series of image processing steps are then performed on the image 32. The image processing steps include systematic background suppression 34, image deconvolution 36, image segmentation 38, and a decision analysis block 40. The image processing steps render a series of extracted ultrasonic images, as each preceding image is subsequently processed through a subsequent step. It will be appreciated that these image processing steps can be implemented adaptively by updating the noise models and estimates after each new data collection (imaging) activity.

Noise Modeling

Noise modeling, as noted above, forms part of the automatic defect detection methodology. Reliability and robustness of the methodology is improved by the quality of the characterized noise and distortion. As FIG. 2 depicts, the methodology disclosed herein accounts for three types of noise and distortion—systematic noise 42 (systematic error), random noise 46 e.g. speckle, and image distortion or blurring e.g. convolution of the signal with the system point spread function 44 (PSF). Each source of image error is preferably modeled separately, as will now be described.

Systematic Noise Model

Figure 3:
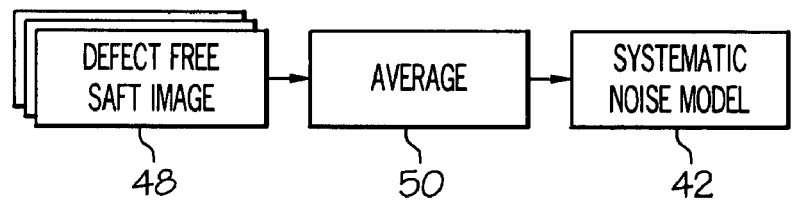
FIG. 3 is a functional block diagram of a systematic noise modeling algorithm.

Systematic noise can be caused by spurious return signals due to interaction between wedge, transducer and sample interfaces, specimen geometry constraints and systematic errors introduced by the signal source and receiver. The preferred approach to the systematic background modeling is depicted schematically in FIG. 3. For systematic error assignment, a number of undamaged plate baseline samples 48 may be scanned, and the error may be determined by averaging 50 over the set of input images. An expected value at any point in the image is given by $$E(\phi) = \frac{1}{N} \sum_{i=1}^{N} \phi_i,$$

where N is the total number of the baseline samples.

Since random error is suppressed by averaging, after sufficient averaging of images from similar undamaged plates, the true value of every point in the image should be zero. Therefore any remaining value in the averaged image is systematic error, $b(\phi)$ referred to herein as bias.

Systematic Background Suppression

Systematic error may be removed by means of subtraction of the model for the systematic noise from the SAFT image of the specimen under investigation. This may be represented by the following:

$$\phi = \phi_{SAFT} - b(\phi),$$

where $\phi$ is a true image value, $\phi_{SAFT}$ is an observed SAFT image and $b(\phi)$ is the systematic error (bias). The foregoing expression can be referred to as a systematic background noise suppression algorithm. It will be appreciated that the bias may depend on the experimental configuration, i.e. transducer type, transducer mounting wedge shape, size and material, ultrasound pulse shape, Lamb wave propagation mode, test specimen material and dimension, etc. Therefore, it should be determined separately, on a case-by-case basis, for each unique configuration.

In one exemplary embodiment, to determine the systematic background noise, non-damaged plate samples are scanned with shear velocity, longitudinal velocity and thickness given respectively by, $V_s$ of about 3140 m/s, $V_1$ of about 5680 m/s, and d of about 1.82 mm. A linear piezo-ceramics transducer array with central frequency 2.5 MHz is used to scan the specimens.

Figure 4:
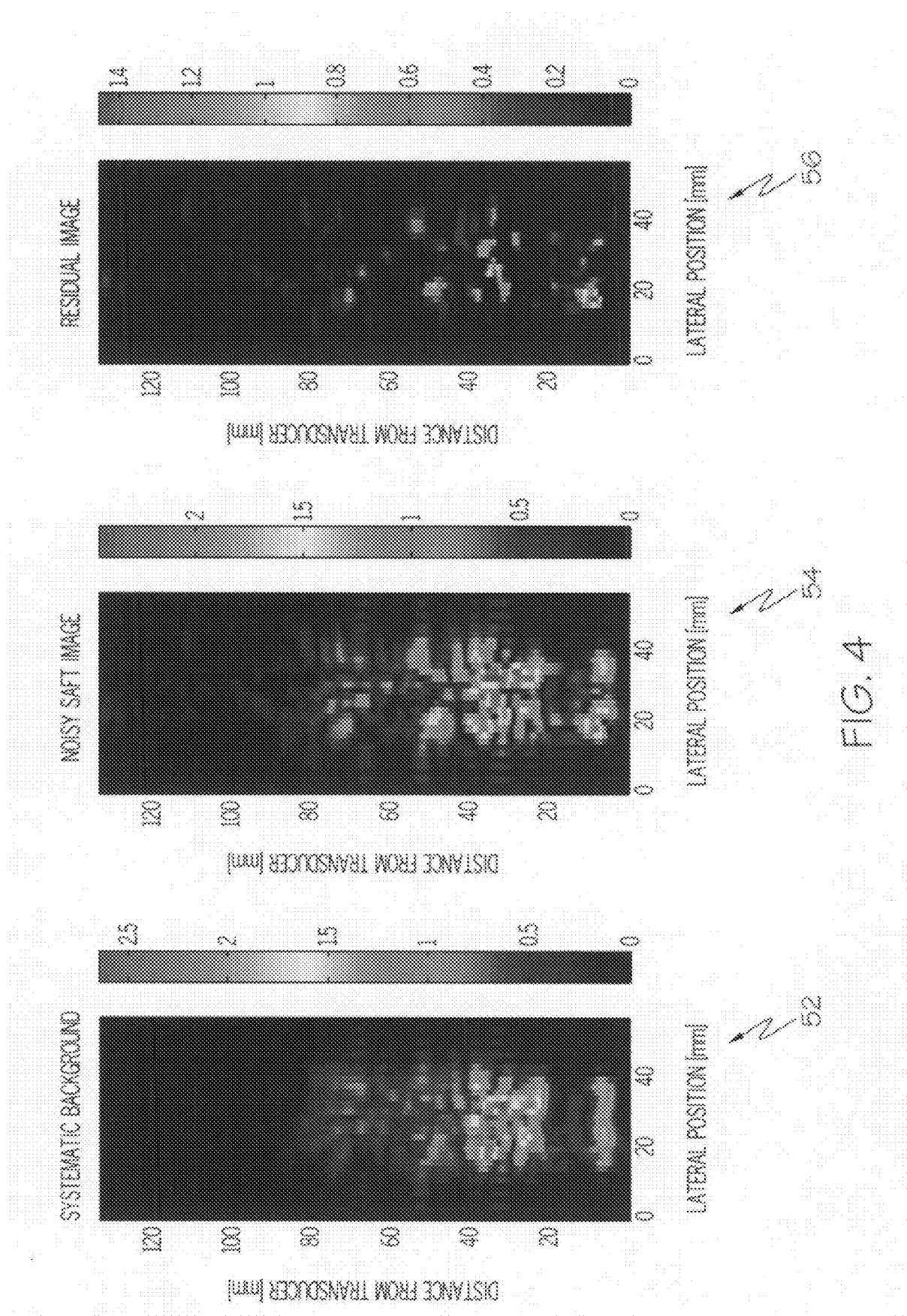
FIG. 4 depicts an exemplary systematic background model and a subtraction from a SAFT image.

FIG. 4 shows results of the systematic background determination and its subtraction from an example of L-SAFT processed image, pursuant to a systematic background noise suppression algorithm. As described above, the background noise suppression algorithm may incorporate one or more mathematical models representing systematic noise. In FIG. 4, the data were analyzed using an A1 Lamb wave propagation mode. Image 52 shows an exemplary special distribution of the bias. Throughout the following images in FIG. 4, the Y axis represents a distance from the transducer 24 in millimeters, as the X axis represents a lateral position across a portion of sampled surface in millimeters. Image 54 shows an exemplary noisy L-SAFT processed image. Finally, image 56 shows a residual image from the distribution of image 52 subtracted from the image 54.

Point Spread Function

Figure 5:
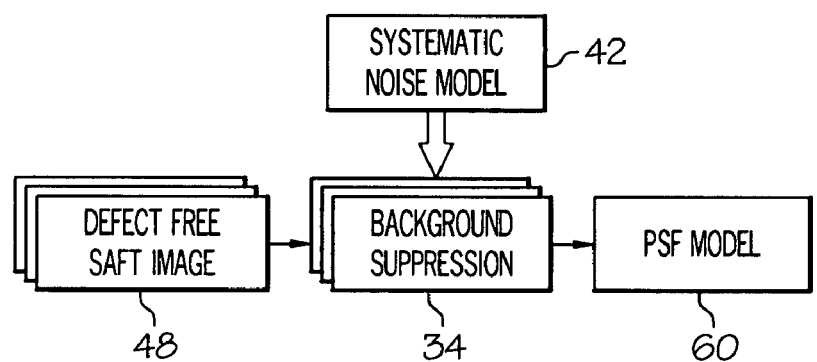
FIG. 5 is a functional block diagram of a method for estimating the point spread function from a known set of SAFT images.

A point spread function (PSF) of the system can be modeled based on the physical principals of the image system, measured, or estimated directly from known SAFT image data. The processing chain used to estimate the PSF model from defect free SAFT images is depicted in FIG. 5. Here again, a number of defect free SAFT images 48 are introduced. A systematic noise model 42 is brought to bear in a systematic background noise suppression algorithm, the data of which is utilized to generate PSF model 60. The point spread function is used to remove distortion inherent in the SAFT image due to the physical limitations of image formation. As depicted in FIG. 2, the distortion is removed through the application of a linear filtering process known as deconvolution.

Ultrasound images are distorted by several phenomenon in so-called "signal transmission channels". A respective transmission channel comprises tissue/material layers between a transducer and a target and both the analog and the digital part of ultrasound signal processing. The distortion can be modeled using convolution model:

$$y(n) = x(n) \otimes h(n),$$

where y(n) is the distorted signal, x(n) is the original ultrasound signal, and h(n) represents the distortion point spread function (PSF). The deconvolution reduces the effect of the PSF on the measured signal. The deconvolution provides significant enhancement of image segment borders to make subsequent image segmentation easier and more reliable.

One method of estimating the PSF is via a homomorphic filtering method. A homomorphic filter transforms the convolution of two signals into a sum of signals derived from the original ones, as represented by the following equation:

$$\hat{y}(n) = \hat{x}(n) + \hat{h}(n).$$

Figure 6:
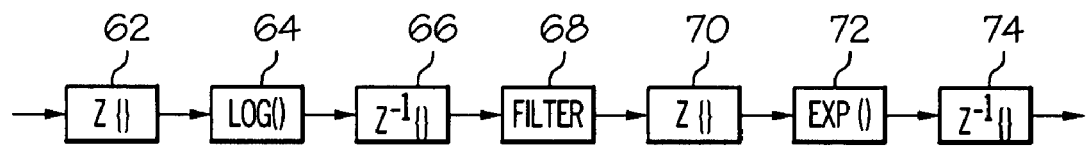
FIG. 6 depicts a homomorphic filtration method.

This method, which was developed originally for deconvolution of radiofrequency (RF), is based on the assumption that the two components of the convolution have different spatial frequency properties. This allows simple low pass filtering in the cepstrum domain to separate the signal (x(n)) from the PSF (h(n)). The principle of the method is depicted in FIG. 6, where a respective signal is first converted by a Z-transform (step 62) into the Z domain. The signal is then processed through a log( ) function (step 64), and then converted back to the time domain by an inverse Z-transform function (step 66). The signal is then processed through a filter (step 68), converted back to the Z domain (step 70), processed through an exp( ) function (step 72), and again converted back to the time domain (step 74).

Figure 7:
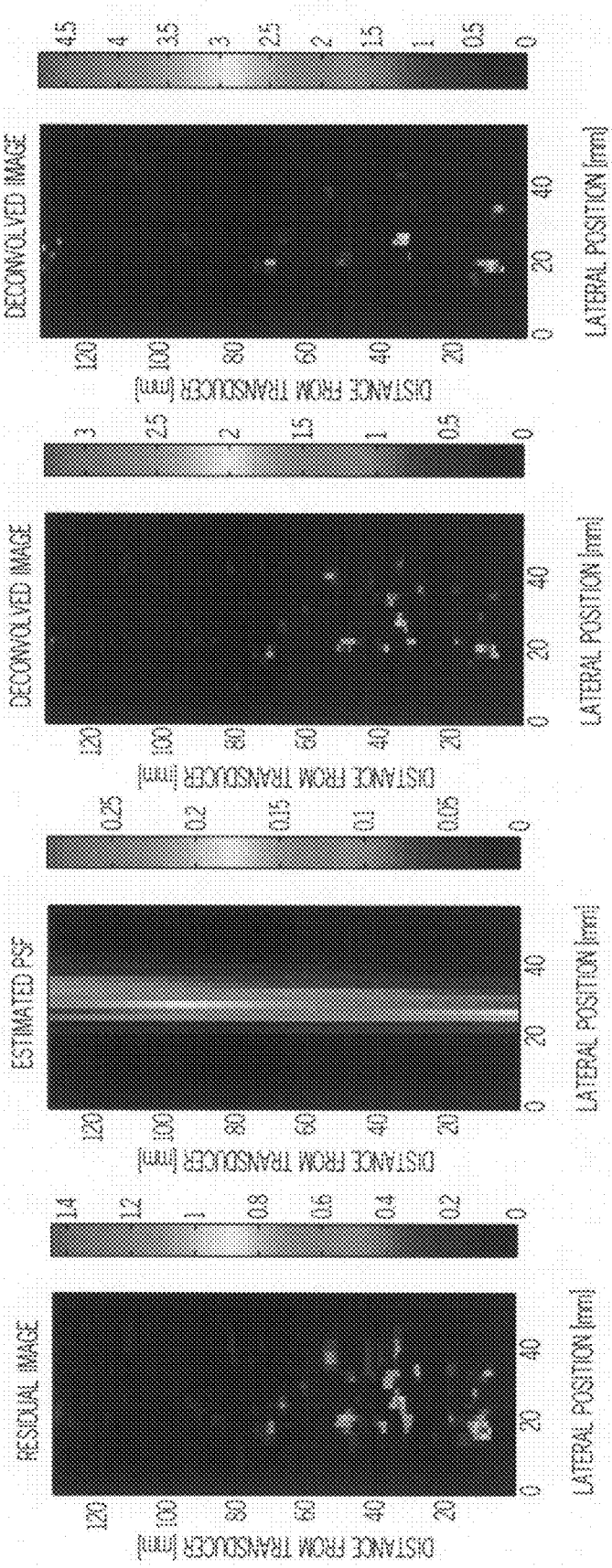
FIG. 7 depicts a SAFT image deconvolution produced using a 1-dimensional PSF estimate and homomorphic filtration.

FIG. 7 illustrates a SAFT deconvolution using PSF estimation by means of homomorphic filtration. Again, as in FIG. 4, the X and Y axes are representative of lateral position and distance from the transducer in millimeters, respectively. Image 76 shows a residual SAFT image. For convenience image 78 shows a simple one dimensional estimate for the PSF. Two dimensional PSF can also be generated. Image 80 shows a deconvolved image using a Lucy-Richardson deconvolution algorithm. A deconvolved image 82 is shown using a Wiener deconvolution.

Random Noise Modeling

The ultrasound SAFT imaging involves the coherent summation of ultrasonic echo signals returned from scatterers that may be located in the sample under investigation. In addition to scattering from defects, scattered returned signals may arise from the random distribution of grain boundaries in metal and/or aggregates in composites and material non-homogeneities, which gives rise to an interference pattern commonly referred to as "speckle." Because it is formed from signals reflected from randomly located scatterers, speckle has a random nature. Due to the statistical nature of the speckle (noise) signal, a statistical analysis approach may be used.

Figure 8:
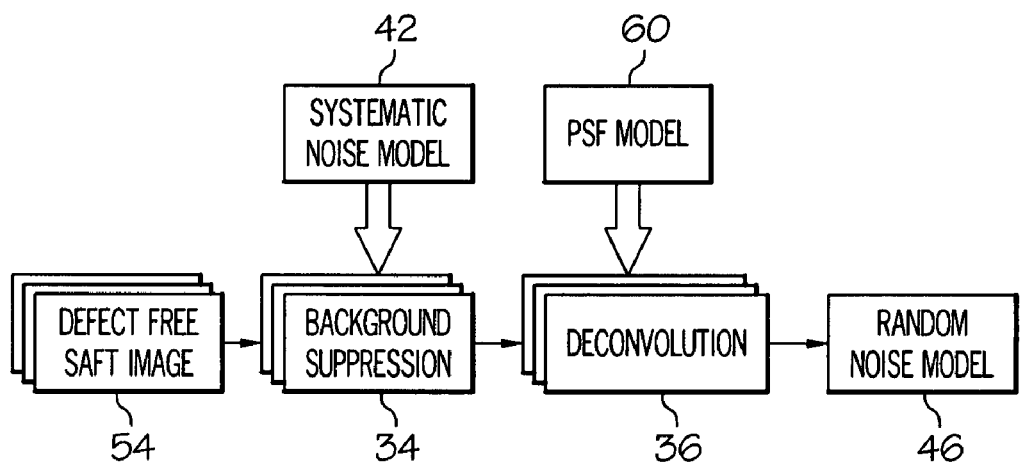
FIG. 8 depicts a random noise modeling method.

An exemplary random noise modeling process is shown in FIG. 8. First, a set of defect free SAFT images 54 are cleared of systematic background noise (incorporating model 42 in a suppression algorithm 34 as previously described). Next, deconvolution 36 is performed to remove convolution distortion from the data. Finally, the remaining random background noise is modeled by a probability density function 46 (PDF). Thus, an estimate of PDF parameters is established for the image pixel values. The random noise model 46 seeks the best fit for the histogram of the ultrasound image data. Due to beam spreading and other physical effects, the PDF characteristics of the random noise can vary with image location. Thus, when needed, the input images may be split into small patches and the PDF parameters are estimated for each local sub-domain of the collected set of images.

Image Fusion

Under certain conditions, such as wide band ultrasonic excitation or by applying various excitation signals to the transducer, the potential exists to generate more than one image using different ultrasonic Lamb wave modes without moving the transducer. For example, ultrasonic synthetic aperture focused images of the inspected area could be generated using data acquired from a symmetric and an antisymmetric Lamb wave mode. For a given material type and thickness, the modes can be separated through frequency bandwidth selection and/or temporal gating prior to the SAFT image reconstruction. Since the set of ultrasonic Lamb wave modes are known to be orthogonal, exhibiting specific characteristics to each mode, e.g. particle displacements, the images from each mode can provide additional information about the nature of the inspected area.

Figure 9:
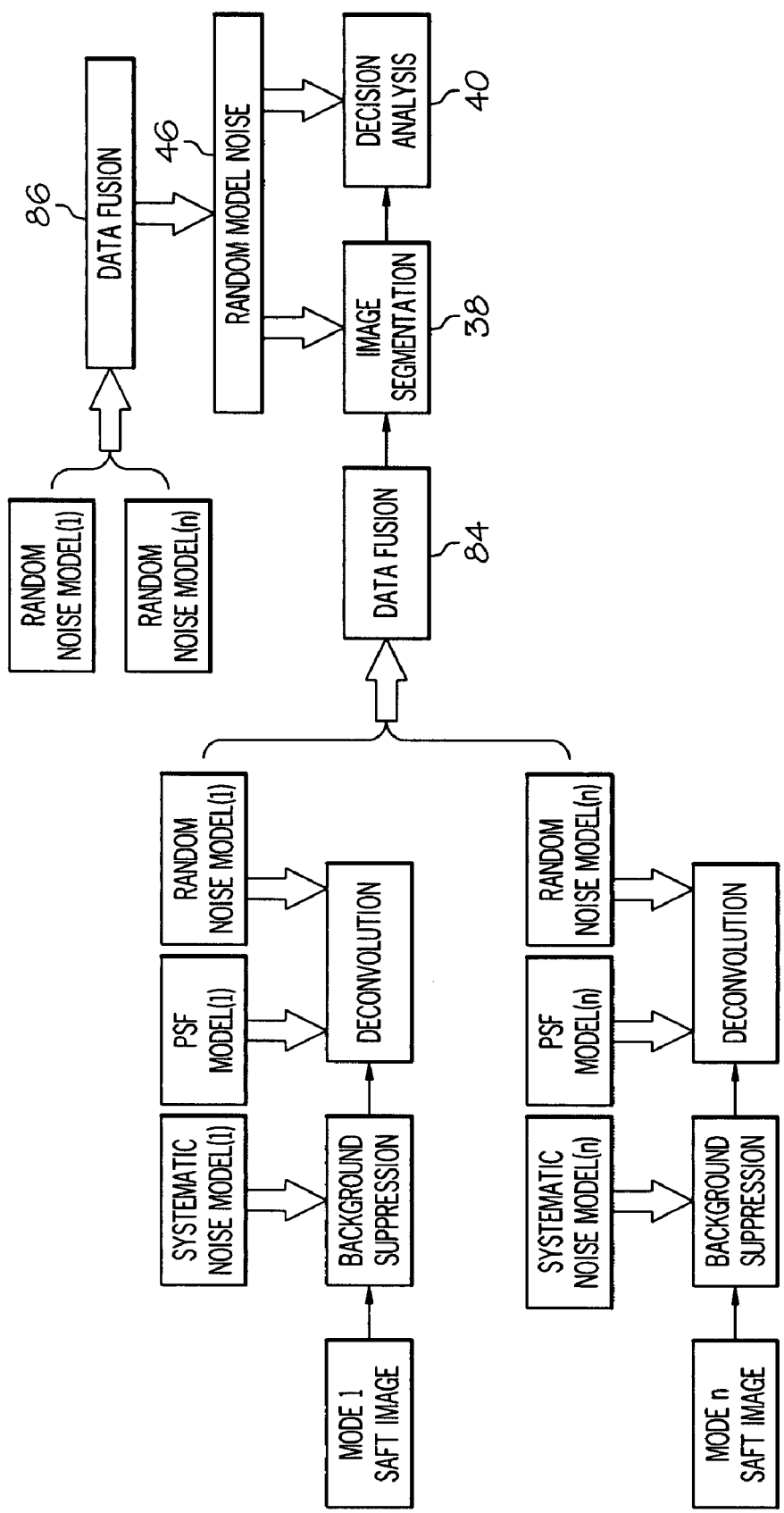
FIG. 9 depicts a method for fusing images from multiple inspection modes.

To combine multiple images acquired using distinct ultrasonic excitation, e.g. different Lamb wave modes, the image fusion process depicted in FIG. 9 may be used. As depicted therein, each imaging mode is studied to establish its own systematic noise model, PSF model, and random noise model. As previously described, this information is established a priori to actual sensor system operation. It will be appreciated that these image processing steps can be implemented adaptively by updating the noise models after each new data collection (imaging) activity. Simplifications can be made by combining noise models for more than one image when variations between commensurate noise models do not change significantly for the different images. Next, the images are processed according to the background suppression and deconvolution steps outlined above to yield multiple unique images of the inspected area. At this stage, there are a variety of data fusion techniques that can be used to fuse the images, such as Bayesian methods, fuzzy logic inference, weighting and voting schemes, Dempster-Shafer methods, and neural network techniques (represented as data fusion 84). Estimates for the statistical measures of the new random noise model associated with the fused image can also be made. This can proceed analytically working with the probability density models for the random background noise and the data fusion methodology or the new random noise model can be estimated empirically through Monte Carlo techniques. As in the discussion above, the random noise model for the combined fused data (represented as data fusion 86) is used in subsequent image segmentation and decision analysis steps.

Image Segmentation

Figure 10:
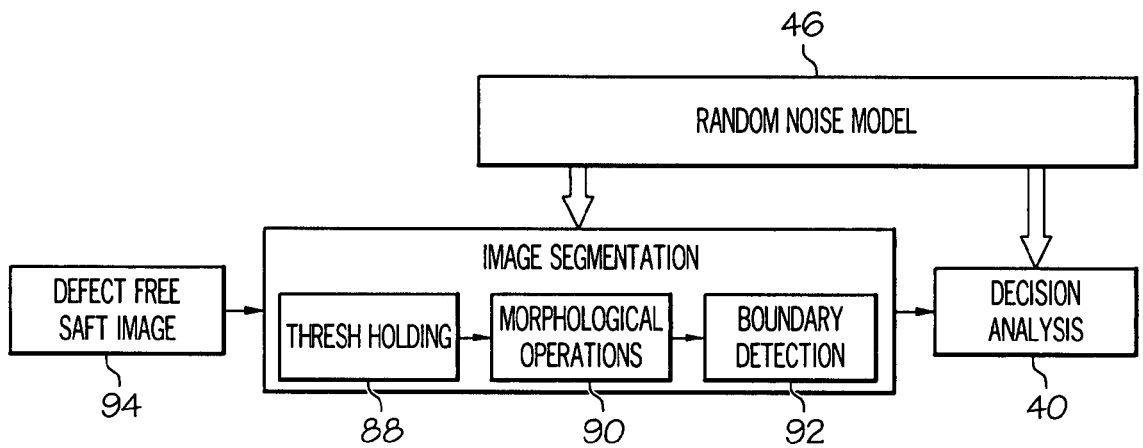
FIG. 10 depicts a method for adaptive segmentation.

An exemplary image segmentation method is depicted in FIG. 10. This depicted method includes adaptive thresholding 88 based on the spatially varying random noise statistics, morphological processing 90 for segment boundaries enhancement, and segment boundary detection 92 which is performed on a processed SAFT image 94. The adaptive image thresholding exploits the previously estimated random noise statistics. In some embodiments the image segmentation method may be performed on an image obtained with guided lamb waves.

Figure 11:
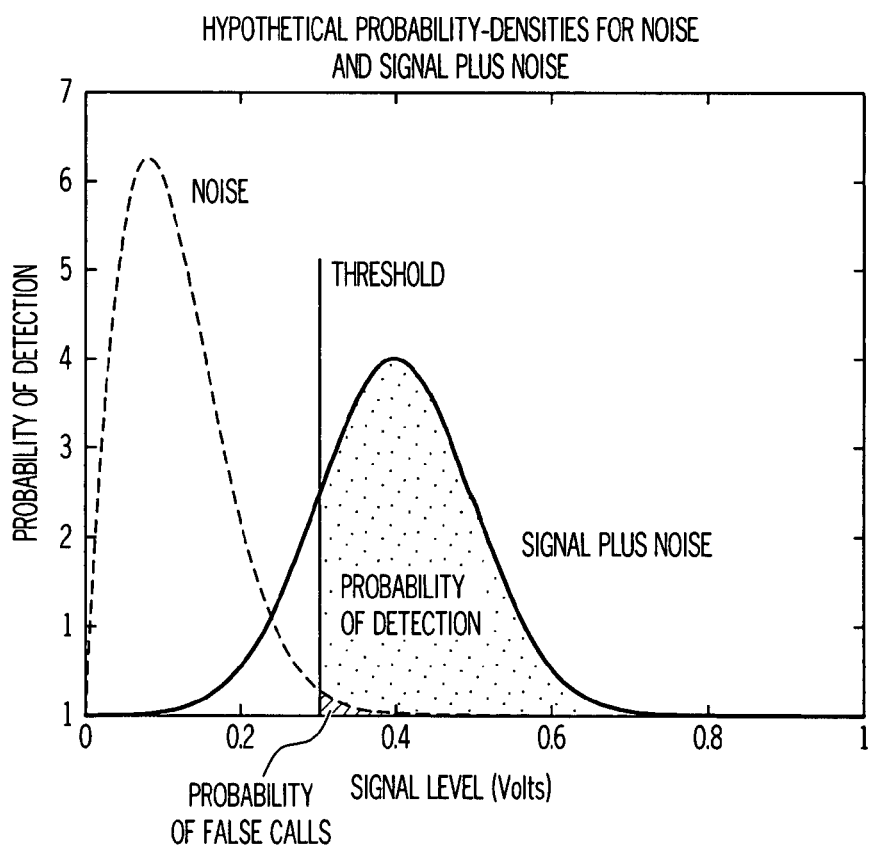
FIG. 11 depicts a method of setting a threshold value to achieve certain PFI and POD rates.

FIG. 11 depicts an exemplary method of setting the image threshold level to achieve a given PFI. The probability of detection for a noise distribution and signal plus noise distribution are shown as functions of signal level. The probability that the amplitude of a pixel exceeds a threshold when no signal is present is the probability of false calls or probability of false indication. The image 'detector' threshold level is set to limit the probability of detecting the noise to an acceptable level. This false call probability, $P_{fc}$, can be determined from:

$$P_{fc} = \int_{V_t}^{\infty} p_n(x)dx$$
$$= \int_{0}^{\infty} p_n(x)dx - \int_{0}^{V_t} p_n(x)dx$$

where $p_n$ is the probability-density function of the noise, and $V_t$ is the threshold value.

As previously described the random noise can be determined and modeled throughout the image. Furthermore the signal responses for a specific defect can be modeled. After giving consideration to the randomizing effects of defect orientation, morphology, and material variability a range of signal responses can be produced. By combining these results with the background noise and threshold criterion estimates of the POD for specific defect, material, transducer configurations can be established.

The main advantage of the above-described approach is that it assures constant false alarm probability ($P_{fa}$) for each anomaly of the image. Moreover, because the distribution parameters can be estimated locally to reflect non-stationarity of the random background noise, the threshold value varies according to image position. This feature allows adaptability of the thresholding algorithm to local properties of the random background noise, which in turn results in higher performance for the thresholding operation.

For example, under certain samples and defect conditions we have found that the distributed noise model is well characterized by locally varying Weibull distributions, representing the random noise data associated with the image. On the basis of the estimated Weibull distribution parameters, the value of the threshold can be determined in order to provide a constant false alarm rate. To evaluate the false alarm probability, $P_{fa}$, we recall the Weibull cumulative probability function:

$$F(x) = 1 - \exp\left[-\frac{x}{\eta}\right]^{\beta}.$$

In this two-parameter Weibull distribution, $\eta$, is a scale parameter or characteristic life and $\beta$ is the shape parameter or slope of the distribution. After substitution and evaluation at the integration limits the probability of false calls at a particular threshold level is:

$$P_{fa} = \exp\left[-\frac{V_t}{\eta}\right]^{\beta},$$

Rearranging, the threshold ($V_T$) necessary to limit the probability of false calls to $P_{fa}$ is:

$$V_t = \eta(-\ln P_{fa})^{\frac{1}{\beta}}.$$

An exemplary method of determining the POD for various defects is to adapt the distance-gain-reflector size (DGS) approach introduced by Krautkramer and others in Germany between 1968 and 1973. This approach models the response of defects to bulk ultrasonic wave inspection foregoing the need for tedious measurements although a measurement approach could used as an alternative. The ultrasonic signal strength returned from a defect is known to depend on material attenuation ($\delta$), beam spreading/focusing, ultrasonic wavelength ($\lambda$), probe dimensions, as well as defect size and shape. A defect form factor (K) is introduced to account for the different types of defects. Calibration curves are generated to relate the acoustic field strength (I) to locations within the radiated field under various reflector beam size relationships. Using these calibration curves the return signal amplitude can be expressed as:

$$\frac{V}{V_o} = K \frac{\lambda^2}{S} I \exp(-2\delta\tau),$$

where Vo is the maximum signal amplitude, S is the probe area, and τ is the distance to the target. In the case of focused Lamb waves, the amplitude, $I(\theta, \tau)$, and waist size, $S(\theta, \tau)$, of the point spread function (PSF) within the near field region of the transducer are established, where θ is the angle of the steered beam and τ is distance. For flaws smaller than the PSF, after accounting for the depth of the flaw (Δ) versus the through thickness (d) nature of the focus Lamb waves, one gets:

$$\frac{V}{V_o} = K\left(\frac{\Delta}{d}\right)\frac{\lambda^2}{S(\theta,\tau)} I(\theta, \tau)\exp(-2\delta\tau).$$

POD estimates can be made for a given flaw inspection scenario by combining the estimates of the background noise and a threshold criterion with calculated signal responses from the calibration curves. For a given flaw size and location a range of responses can be parametrically established by randomizing the defect orientation, morphology, and material variability parameters.

Next, morphological operators can be applied to the thresholded image, if desired. The object of the morphological operator is to remove salt and pepper noise and to further smooth the segments boundaries for better defect edge definition. The size of the structuring element used in the morphological processing is set by the relationship between the size of the smallest anomaly that it is desired to detect, and resolution and rendering limitations. The last step of the image segmentation is boundary detection. The goal is to find a coherent one-dimensional boundary features from the individually identified defects with local edge pixels. Several common methods based on the morphological operators and gradient operators of the first or second order may be used to achieve this step.

Figure 12:
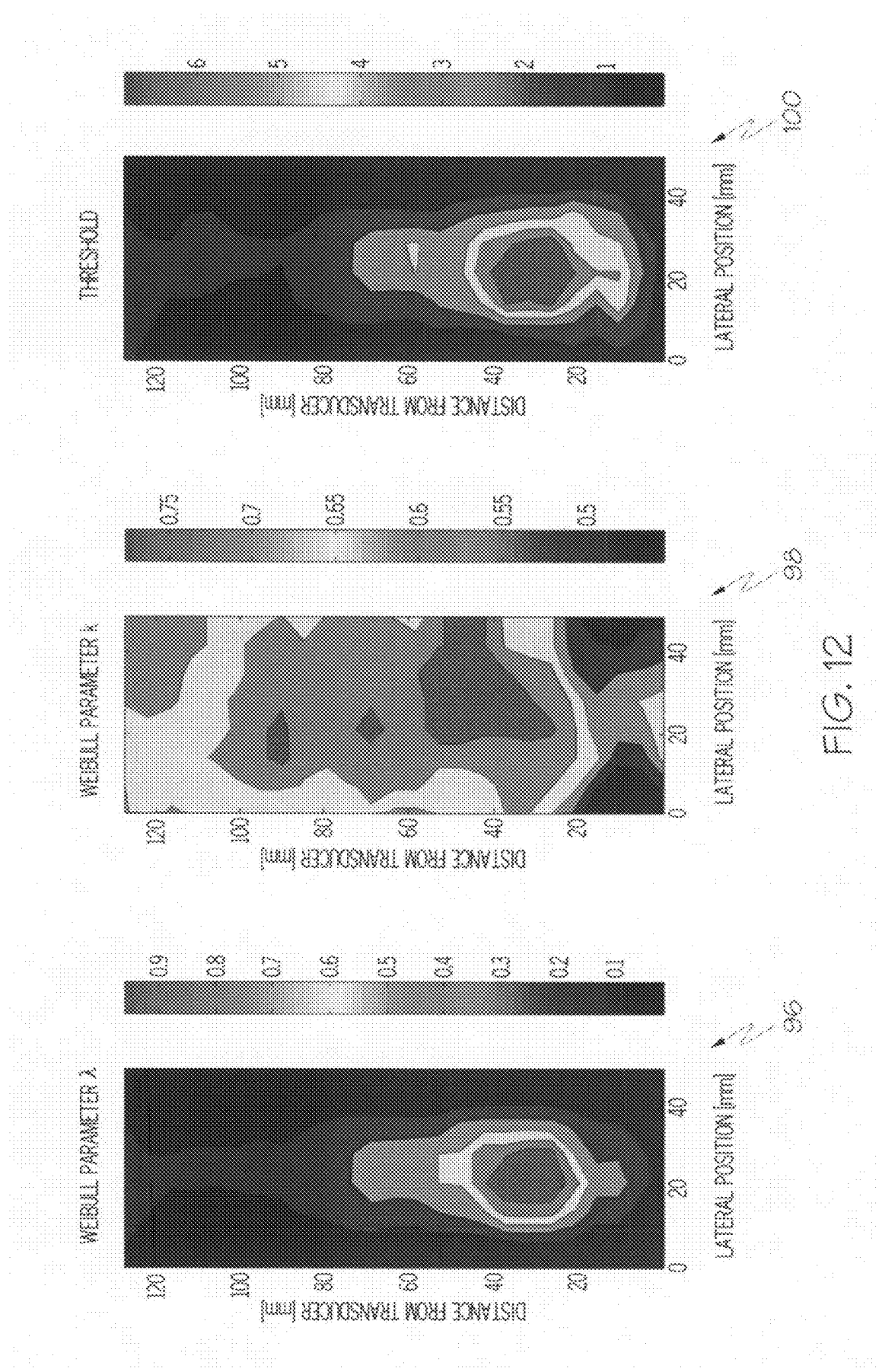
FIG. 12 depicts exemplary smooth contour estimates for locally varying Weibull distribution parameters.

FIG. 12 shows exemplary smooth contour estimates for locally varying Weibull distribution parameters, with the accompanying X and Y axis designations of FIGS. 4 and 7. Image 96 shows a representation of a scale parameter. Image 98 shows a representation of a shape parameter. Finally, image 100 shows an exemplary threshold value distribution obtained using the Weibull parameters shown in images 96 and 98.

Figure 13:
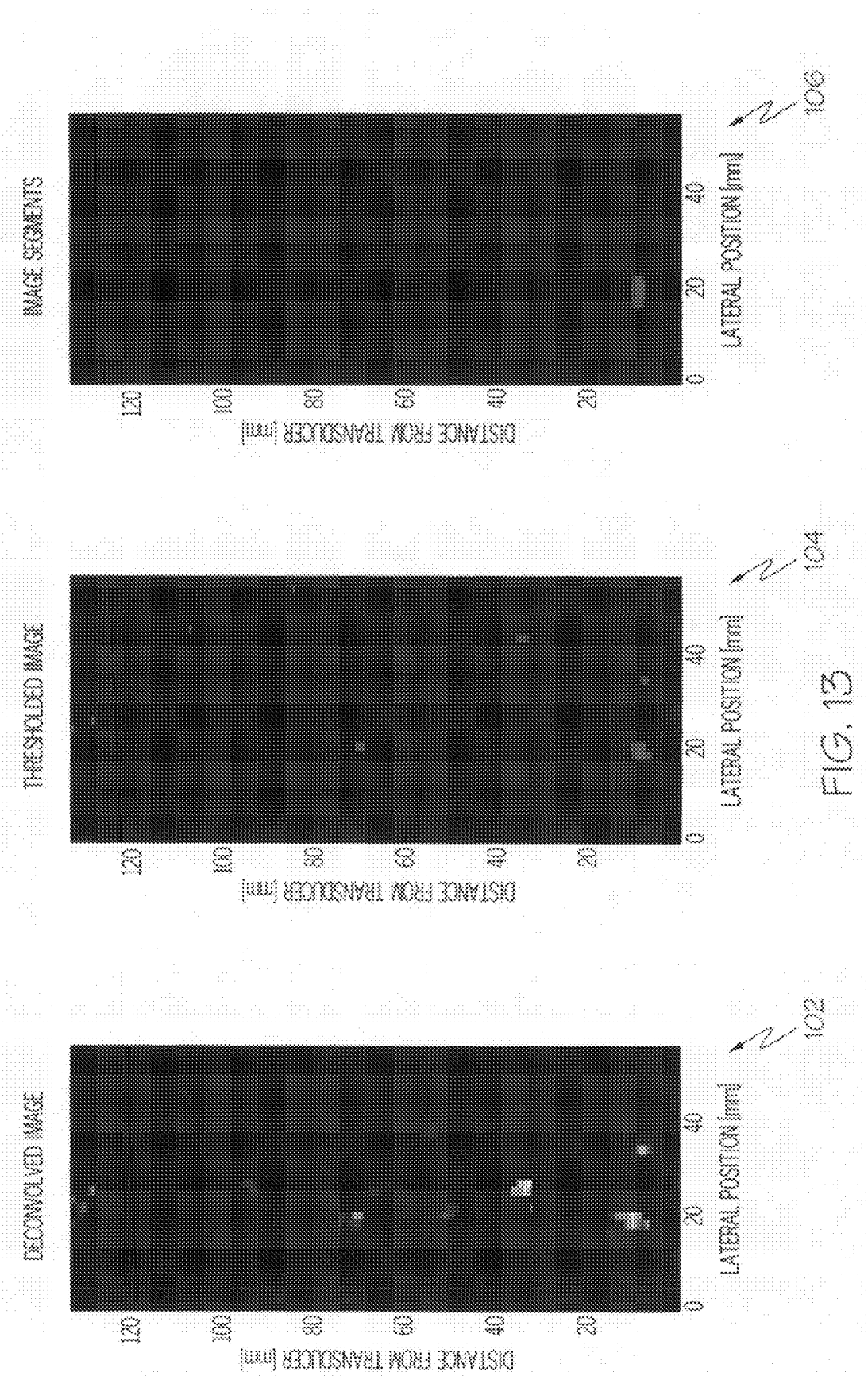
FIG. 13 depicts an exemplary result of an image segmentation technique.

FIG. 13 shows an exemplary result of an image segmentation technique, again with the accompanying X and Y axis designations of FIGS. 4, 7, and 12. Image 102 illustrates a deconvolved SAFT image. Image 104 illustrates a thresholded image. Finally, image 106 illustrates a resultant image following morphological processing 90 and edge boundary detection 92. In the depicted embodiment, a Canny edge detection operator is utilized to segment respective areas. The contours shown in FIG. 13 are filled for better visualization and distinction.

Feature Description

An optional feature description step follows the image segmentation process. Every identified image segment can be described by a set of parameters that quantitatively express its properties. Selection of appropriate statistics/parameters can be helpful in discrimination between regions that represent false signals and true defect damage. Furthermore, it can provide information about severity and advancement of the damage.

The selection of effective features is domain dependant. The features used to distinguish between for example corrosion pitting and stress corrosion cracking will, in most cases, not be identical. However once a representative set of defect samples have been studied, and the features extracted, there are a number of techniques to help with feature selection. The idea is to find distinguishing characteristics of the data sets that are invariant to irrelevant transformations and insensitive to noise. To accomplish this, feature selection is usually undertaken in coordination and iteratively along with the design of a classifier.

Clustering algorithms are classic techniques to transform feature vectors from the measured parameters into a feature space where class identification can take place. The goal of pattern classification is to assign a physical object or process to a pre-defined class based on the statistics of its features. Various transformations such as principal component analysis, Sammon mapping, and other non-linear transformations can be used, while designing a classifier through techniques such as Fisher discriminant analysis. For example, features such as length of segment boundaries and average segment areas are simple geometric features. More sophisticated feature extraction could involve curve analysis. The segment boundaries can be modeled as a parametrical curve (circle, ellipse, etc.) or as a nonparametrical curve (principal curve). Segment properties can be described by statistical means using statistical moments of the first and higher order. Next, different means of gradient computation can be used if needed.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention.

What is claimed is:

1. An automated method for detecting and displaying corrosion or crack defects in an object by a computer on a display, comprising:
    obtaining a first of a plurality of ultrasound images of the object acquired with guided Lamb waves generated by a transducer;
    processing the first image of the object by the computer using a synthetic aperture focusing technique (SAFT) to enhance a resolution and a signal to noise ratio of a first extracted ultrasonic image of the object;
    applying a systemic background noise suppression algorithm to the first extracted ultrasonic image of the object by the computer to generate a second extracted ultrasonic image of the object having reduced noise; and
    applying a deconvolution linear filtering process by the computer to the second extracted ultrasonic image of the object to render a third extracted ultrasonic image of the object on the display.

2. The method of claim 1, wherein the plurality of ultrasound images is acquired using distinct ultrasonic excitation or filtering a frequency content of a return ultrasonic signal to employ a plurality of Lamb wave modes.

3. The method of claim 2, further including combining the first image with an additional image of the plurality of ultrasound images to render a composite image.

4. The method of claim 3, further including processing the composite image thorough an image segmentation algorithm.

5. The method of claim 4, wherein processing the composite image through an image segmentation algorithm further includes applying a voltage threshold algorithm determined from a statistical noise model for image data.

6. The method of claim 4, wherein processing the composite image through an image segmentation algorithm further includes applying a voltage threshold algorithm according to $$V_t = \eta(-\ln P_{fa})^{\frac{1}{\beta}},$$

where $V_t$ is a voltage threshold, $\eta$ is a scale parameter or characteristic life, $\beta$ is a shape parameter or slope of the Weibull distribution, and $P_{fa}$ is a probability of false calls.

7. The method of claim 4, wherein processing the composite image thorough an image segmentation algorithm incorporates a mathematical model representing random noise.

8. The method of claim 4, wherein processing the composite image thorough an image segmentation algorithm incorporates a mathematical model representing the probability of detecting a defect.

9. The method of claim 3, wherein combining the first image with the additional image further includes employing a Bayesian method, fuzzy logic inference, weighting and voting scheme, Dempster-Shafer method, or a neural network technique.

10. The method of claim 1, wherein the first image is processed thorough an image segmentation algorithm.

11. The method of claim 10, wherein processing the first image through an image segmentation algorithm further includes applying a voltage threshold algorithm determined from a statistical noise model for image data.

12. The method of claim 11, wherein processing the first image through an image segmentation algorithm further includes applying a voltage threshold algorithm according to $$V_t = \eta(-\ln P_{fa})^{\frac{1}{\beta}},$$

where $V_t$ is a voltage threshold, $\eta$ is a scale parameter or characteristic life, $\beta$ is a shape parameter or slope of the Weibull distribution, and $P_{fa}$ is a probability of false calls.

13. The method of claim 1, wherein applying the systemic background noise suppression algorithm to the first extracted ultrasonic image further incorporates a mathematical model representing systematic noise.

14. The method of claim 1, wherein applying the deconvolution linear filtering process incorporates a point spread function (PSF) estimated from a plurality of defect-free SAFT images.

15. An automated defect detection system, comprising:
a transducer configured for obtaining a first of a plurality of ultrasound images acquired with guided Lamb waves; and
a controller coupled to the transducer configured to processes the first image using a synthetic aperture focusing technique (SAFT) to render a first extracted ultrasonic image, apply a systemic background noise suppression algorithm to the first extracted ultrasonic image to render a second extracted ultrasonic image, and apply a deconvolution linear filtering process to the second extracted ultrasonic image to render a third extracted ultrasonic image.

16. The system of claim 15, wherein the plurality of ultrasound images is acquired using distinct ultrasonic excitation or filtering a frequency content of a return ultrasonic signal to employ a plurality of Lamb wave modes.

17. The system of claim 16, wherein the controller:
combines the first image with an additional image of the plurality of ultrasound images to render a composite image, and processes the composite image thorough an image segmentation algorithm.

18. The system of claim 17, wherein the controller employs a Bayesian method, fuzzy logic inference, weighting and voting scheme, Dempster-Shafer method, or a neural network technique to combine the first image with the additional image.

19. The system of claim 17, wherein the controller applies a voltage threshold determined from a statistical noise model for image data.

20. The system of claim 17, wherein the controller applies a voltage threshold algorithm according to $$V_t = \eta(-\ln P_{fa})^{\frac{1}{\beta}},$$

where $V_t$ is a voltage threshold, $\eta$ is a scale parameter or characteristic life, $\beta$ is a shape parameter or slope of the distribution, and $P_{fa}$ is a probability of false calls.

21. The system of claim 16, wherein the controller incorporates a mathematical model representing systematic noise to apply the systemic background noise suppression algorithm to the first image.

22. The system of claim 16, wherein the controller incorporates a point spread function (PSF) estimated from a plurality of defect-free SAFT images to apply the deconvolution linear filtering process.

23. The system of claim 16, wherein the controller incorporates a mathematical model representing random noise to process the composite image thorough an image segmentation algorithm.

24. The system of claim 16, wherein the controller incorporates a mathematical model representing the probability of detecting a defect.

25. A computer program product for performing automated defect detection of an object, the computer program product comprising a computer-readable storage medium having computer-readable program code portions stored therein, the computer-readable program code portions comprising:
a first executable portion for obtaining a first of a plurality of ultrasound images of the object acquired with guided Lamb waves;
a second executable portion for processing the first image using a synthetic aperture focusing technique (SAFT) to generate a first extracted ultrasonic image of the object;
a third executable portion for applying a systemic background noise suppression algorithm to the first extracted ultrasonic image to generate a second extracted ultrasonic image of the object; and a fourth executable portion for applying a deconvolution linear filtering process to the second extracted ultrasonic image to render a third extracted ultrasonic image of the object on a display.

26. The computer program product of claim 25, further including:

a fifth executable portion for combining the first image with an additional image of the plurality of ultrasound images to render a composite image; and a sixth executable portion for processing the composite image thorough an image segmentation algorithm.

* * * * *

UNITED STATES PATENT AND TRADEMARK OFFICE
CERTIFICATE OF CORRECTION

| | | |
|---|---|---|
| PATENT NO. | : 7,783,433 B2 | Page 1 of 1 |
| APPLICATION NO. | : 11/880450 | |
| DATED | : August 24, 2010 | |
| INVENTOR(S) | : Gordon et al. | |

It is certified that error appears in the above-identified patent and that said Letters Patent is hereby corrected as shown below:

Column 11, lines 7, 24, 27, and 36, "thorough" should be changed to --through--;
    Column 12, lines 14 and 46, "thorough" should be changed to --through--;
    Column 14, line 5, "thorough" should be changed to --through--.

Signed and Sealed this

Twenty-third Day of November, 2010

David J. Kappos
*Director of the United States Patent and Trademark Office*